United States Patent [19]
Niebur et al.

[11] Patent Number: 5,491,290
[45] Date of Patent: Feb. 13, 1996

[54] HYBRID CORN PLANT AND SEED (3525)

[75] Inventors: William S. Niebur, Victor, France; Loren J. Hoffbeck, Tipton, Ind.; Terrill E. Williams, New Holland, Pa.

[73] Assignee: Pioneer Hi-Bred International, Inc., Des Moines, Iowa

[21] Appl. No.: 286,101

[22] Filed: Aug. 4, 1994

Related U.S. Application Data

[63] Continuation of Ser. No. 831,232, Feb. 3, 1992, abandoned.

[51] Int. Cl.$^6$ .............................. A01H 1/00; A01H 5/00; C12N 5/04
[52] U.S. Cl. .................. 800/200; 800/250; 800/DIG. 56; 47/58; 435/240.4; 435/240.49; 435/240.5
[58] Field of Search ..................... 800/200, 205, 800/DIG. 56, 235, 250; 47/58.03, 58.05; 435/240.4, 240.49, 240.45, 240.5

[56] References Cited

U.S. PATENT DOCUMENTS 4,731,499  3/1988  Puskaric et al. ................. 800/200
5,320,961  6/1994  Zhong et al. .
5,322,789  6/1994  Genovesi et al. .

OTHER PUBLICATIONS

Phillips et al. "Corn & Corn Improvement" Chapter #5 Cell/Tissue Culture & In Vitro Manipulation. AsA publisher #18, pp. 345–387.
Meghji et al. (1984) Crop Science vol. 24. pp. 545–549.

*Primary Examiner*—Gary Benzion
*Attorney, Agent, or Firm*—Pioneer Hi-Bred International, Inc.

[57] ABSTRACT

According to the invention, there is provided a hybrid corn plant, designated as 3525, produced by crossing two Pioneer Hi-Bred International, Inc. proprietary inbred corn lines. This invention thus relates to the hybrid seed 3525, the hybrid plant produced from the seed, and variants, mutants, and trivial modifications of hybrid 3525. This hybrid is a tall, high yielding hybrid that is widely adapted and is excellent for grain and silage production. 3525 is characterized by having an early blacklayer, but flowers late. It is a tall statured hybrid with high ear placement and has excellent stress tolerance.

5 Claims, No Drawings

HYBRID CORN PLANT AND SEED (3525)

This application is a continuation of application Ser. No. 07/831,232, filed Feb. 3, 1992, now abandoned.

FIELD OF THE INVENTION

This invention is in the field of plant breeding, specifically hybrid corn breeding.

BACKGROUND OF THE INVENTION

The goal of plant breeding is to combine in a single variety/hybrid various desirable traits of the parental lines. For field crops, these traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, maturity, and fruit size, is important.

Field crops are bred through techniques that take advantage of the plant's method of pollination. A plant is self-pollinating if pollen from one flower is transferred to the same or another flower of the same plant. A plant is cross-pollinated if the pollen comes from a flower on a different plant.

Plants that have been self-pollinated and selected for type for many generations become homozygous at almost all gene loci and produce a uniform population of true breeding progeny. A cross between two homozygous lines produces a uniform population of hybrid plants that may be heterozygous for many gene loci. A cross of two plants each heterozygous at a number of gene loci will produce a population of hybrid plants that differ genetically and will not be uniform.

Corn plants (*Zea mays* L.) can be bred by both self-pollination and cross-pollination techniques. Corn has male flowers, located on the tassel, and female flowers, located on the ear, on the same plant. Natural pollination occurs in corn when wind blows pollen from the tassels to the silks that protrude from the tops of the incipient ears.

The development of corn hybrids requires the development of homozygous inbred lines, the crossing of these lines, and the evaluation of the crosses. Pedigree breeding and recurrent selection breeding methods are used to develop inbred lines from populations. Breeding programs combine desirable traits from two or more inbred lines or various broad-based sources into breeding pools from which new inbred lines are developed by selfing and selection of desired phenotypes. The new inbreds are crossed with other inbred lines and the hybrids from these crosses are evaluated to determine which have commercial potential.

Pedigree breeding starts with the crossing of two genotypes, each of which may have one or more desirable characteristics that is lacking in the other or which complement the other. If the two original parents do not provide all of the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced. $F_1 \rightarrow F_2; F_2 \rightarrow F_3; F_3 \rightarrow F_4; F_4 \rightarrow F_5$, etc.

A hybrid corn variety is the cross of two inbred lines, each of which may have one or more desirable characteristics lacked by the other or which complement the other. The hybrid progeny of the first generation is designated $F_1$. In the development of hybrids only the $F_1$ hybrid plants are sought. The $F_1$ hybrid is more vigorous than its inbred parents. This hybrid vigor, or heterosis, can be manifested in many ways, including increased vegetative growth and increased yield.

The development of a hybrid corn variety involves three steps: (1) the selection of superior plants from various germplasm pools; (2) the selfing of the superior plants for several generations to produce a series of inbred lines, which although different from each other, breed true and are highly uniform; and (3) crossing the selected inbred lines with unrelated inbred lines to produce the hybrid progeny ($F_1$). During the inbreeding process the vigor of the lines decreases. Vigor is restored when two unrelated inbred lines are crossed to produce the hybrid progeny ($F_1$). An important consequence of the homozygosity and homogeneity of the inbred lines is that the hybrid between any two inbreds will always be the same. Once the inbreds that give the best hybrid have been identified, the hybrid seed can be reproduced indefinitely as long as the homogeneity of the inbred parents is maintained.

A single cross hybrid is produced when two inbred lines are crossed to produce the $F_1$ progeny. A double cross hybrid, is produced from four inbred lines crossed in pairs (A×B and C×D) and then the two $F_1$ hybrids are crossed again (A×B)× (C×D). Much of the hybrid vigor exhibited by $F_1$ hybrids is lost in the next generation ($F_2$). Consequently, seed from hybrid varieties is not used for planting stock.

Hybrid corn seed can be produced by manual detasseling. Alternate strips of two inbred varieties of corn are planted in a field, and the pollen-bearing tassels are removed from one of the inbreds (female). Providing that there is sufficient isolation from sources of foreign corn pollen, the ears of the detasseled inbred will be fertilized only from pollen from the other inbred (male), and the resulting seed is therefore hybrid and will form hybrid plants.

The laborious detasseling process can be avoided by using cytoplasmic male-sterile (CMS) inbreds. Plants of a CMS inbred are fertilized with pollen from another inbred that is not male-sterile. Pollen from the second inbred can contribute genes that make the hybrid plants male-fertile. Usually seed from detasseled normal corn and CMS produced seed of the same hybrid is blended to insure that adequate pollen loads are available for fertilization when the hybrid plants are grown.

Corn is an important and valuable field crop. Thus, a continuing goal of plant breeding is to develop stable high yielding corn hybrids that are agronomically sound. The reasons for this goal are obvious: to maximize the amount of grain produced on the land used and to supply food for both animals and humans.

SUMMARY OF THE INVENTION

According to the invention, there is provided a hybrid corn plant, designated as 3525, produced by crossing two Pioneer Hi-Bred International, Inc. proprietary inbred corn lines. This invention thus relates to the hybrid seed 3525, the hybrid plant produced from the seed, and variants, mutants, and trivial modifications of hybrid 3525. This hybrid is a tall, high yielding hybrid that is widely adapted and is excellent for grain and silage production. 3525 is characterized by having an early blacklayer, but flowers late. It is a tall statured hybrid with high ear placement and has excellent stress tolerance.

DEFINITIONS

In the description and examples that follow, a number of terms are used herein. In order to provide a clear and consistent understanding of the specification and claims, including the scope to be given such terms, the following definitions are provided:

ABS= ABSOLUTE MEASUREMENT. The percent (%) mean is the percentage of mean for the experiments in which the hybrid was grown.

ADVANTAGE= The advantage of the hybrid to be patented compared to another hybrid for yield (bushels per acre), moisture (drier is an advantage), income, population, stand (absence of stalk lodging is an advantage), roots (absence of root lodging is an advantage), and test weight, respectively, in strip tests.

BAR PLT= BARREN PLANTS. The percent of plants per plot that were not barren (lack ears).

B/STK=BRITTLE STALKS RATING. A 1–9 rating where a 1, 5, and 9 represent serious, average, and little or no potential for brittle stalk breakage.

BRT STK= BRITTLE STALKS. A measure of the stalk breakage near the time of pollination, and an indication of whether a hybrid would snap or break near the time of flowering under severe winds. Data are presented as percentage of plants that did not snap.

BU ACR=YIELD (BUSHELS/ACRE). Actual yield of the grain at harvest adjusted to 15.5% moisture.

D/D= DRYDOWN. This represents the relative rate at which a hybrid will reach acceptable harvest moisture compared to other hybrids on a 1–9 rating scale. A high score indicates a hybrid that dries relatively fast while a low score indicates a hybrid that dries slowly.

D/E=DROPPED EARS RATING. This is a 1–9 rating where a 1, 5, and 9 represent serious, average, and little or no ear droppage potential, respectively.

DRP EAR=DROPPED EARS. This is a measure of the number of dropped ears per plot and represents the percentage of plants that did not drop ears prior to harvest.

D/T= DROUGHT TOLERANCE. This represents a 1–9 rating for drought tolerance, and is based on data obtained under stress conditions. A high score indicates good drought tolerance and a low score indicates poor drought tolerance.

E/HT= EAR HEIGHT RATING. A 1–9 rating with 1, 5, and 9 representing a very low, average, and very high ear placement, respectively.

EAR HT= EAR HEIGHT. The ear height is a measure from the ground to the highest placed developed ear node attachment and is measured in inches.

EST CNT= EARLY STAND COUNT. This is a measure of the stand establishment in the spring and represents the number of plants that emerge on a per plot basis for the hybrid.

GDU BL=GDU TO BLACKLAYER. This is the number of growing degree units required for the hybrid to reach blacklayer from the time that it was planted. Growing degree units are calculated by the Barger Method, where the heat units for a 24-hour period are:

$$GDU = \frac{(Max. + Min.)}{2} - 50$$

The highest maximum used is 86° F. and the lowest minimum used is 50° F. For each inbred or hybrid it takes a certain number of GDUs to reach various stages of plant development.

GDU SHD= GDU TO SHED. The number of growing degree units (GDUs) or heat units required for a hybrid to have approximately 50 percent of the plants shedding pollen and is measured from the time of planting.

GDU SLK= GDU TO SILK. The number of growing degree units required for a hybrid to have approximately 50 percent of the plants with silk emergence from time of planting.

GRN APP= G/A= GRAIN APPEARANCE. This is a 1 to 9 rating for the general quality of the shelled grain as it is harvested based on such factors as the color of the harvested grain, any mold on the grain, and any cracked grain. High scores indicate good grain quality and low scores indicate poor grain quality.

H/POP= YIELD AT HIGH DENSITY. Yield ability at relatively high plant densities on a 1–9 relative rating system with a higher number indicating the hybrid responds well to high plant densities for yield relative to other hybrids. A 1, 5, and 9 would represent very poor, average, and very good yield response, respectively, to increased plant density.

INCOME/ACRE: Relative income per acre assuming drying costs of two cents per point above 15.5 percent harvest moisture and market price of $2.25 per bushel.

L/POP= YIELD AT LOW DENSITY. Yield ability at relatively low plant densities on a 1–9 relative system with a higher number indicating the hybrid responds well to low plant densities for yield relative to other hybrids. A 1, 5, and 9 would represent very poor, average, and very good yield response, respectively, to low plant density.

MST= MOIST= HARVEST MOISTURE. Harvest moisture is the actual percentage moisture of the grain at harvest.

MST RM= MOISTURE RM. This represents the Comparative Relative Maturity Rating (CRM) for the hybrid and is based on the harvest moisture of the grain relative to a standard set of checks of previously determined Comparative RM rating. Linear regression analysis is used to compute this rating.

P/HT= PLANT HEIGHT RATING. This is a 1–9 rating with a 1, 5, and 9 representing a very short, average, and very tall hybrid, respectively.

PLT HT= PLANT HEIGHT. This is a measure of the height of the plant from the ground to the tip of the tassel in inches.

POP K/ACRE: Plants per 0.001 acre.

PERCENT WINS: For yield, moisture, income, populations, stand, roots, and test weight, it would be the percentage of comparisons where the hybrid to be patented yielded more, had lower harvest moisture percentage, had greater income per acre, had better stalks, had better roots, and had higher test weight, respectively, in strip tests.

R/L= ROOT LODGING RATING. A 1–9 rating where a higher score indicates less root lodging potential (1 is very poor, 5 is intermediate, and 9 is very good, respectively, for resistance to root lodging).

ROOT (%): Percentage of plants that did not root lodge (lean greater than 30 degrees from vertical) taken on strip test plots.

RT LDG= ROOT LODGING. Root lodging is the percentage of plants that do not root lodge; plants that lean from the vertical axis at an approximately 30° angle or greater would be counted as root lodged.

S/L=STALK LODGING RATING. This is a 1-9 rating where a higher score indicates less stalk lodging potential (1 is very poor, 5 is intermediate, and 9 is very good, respectively, for resistance to stalk lodging).

SDG VGR= S/VIG=SEEDLING VIGOR. This is the visual rating (1 to 9) of the amount of vegetative growth after emergence at the seedling stage (approximately five leaves). A higher score indicates better vigor and a low score indicates poorer vigor.

STA GRN= STGR= STAY GREEN. Stay green is the measure of plant health near the time of black layer formation (physiological maturity) using a 1-9 visual rating. A high score indicates better late-season plant health and a low score indicates poor plant health.

STAND (%): Percentage of plants that did not break (lodge) below the ear taken on strip test plots.

STK LDG=STALK LODGING. This is the percentage of plants that did not stalk lodge (stalk breakage) as measured by either natural lodging or pushing the stalks and determining the percentage of plants that break below the ear.

T/WT= TEST WEIGHT RATING. This is a 1-9 relative rating with a 1, 5, and 9 indicating very low, average, and very high test weight, respectively.

TST WTA= TEST WEIGHT. The measure of the weight of the grain in pounds for a given volume (bushel) adjusted for percent moisture.

YLD=YIELD FOR MATURITY. This represents a 1-9 rating for a hybrid's yield potential. 1, 5, and 9 would represent very poor, average, and very high yield potential, respectively, relative to other hybrids of a similar maturity.

DETAILED DESCRIPTION OF THE INVENTION

Pioneer Brand Hybrid 3525 is a single cross, yellow endosperm, dent corn hybrid with exceptional yield in its maturity. It has stable yield across a wide range of yield levels, and has excellent stress tolerance. 3525 is a tall statured hybrid with high ear placement.

This hybrid has the following characteristics based on the descriptive data collected primarily at Johnston, Iowa.

In interpreting the foregoing color designations, reference may be had to the Munsell Glossary Book of Color, a standard color reference.

VARIETY DESCRIPTION INFORMATION
HYBRID - PIONEER BRAND 3525
Type: Dent    Region Best Adapted: Central Corn Belt A. Maturity:
  Minnesota Relative Maturity Rating (harvest moisture): 111
  GDU's to Physiological maturity (black layer): 2642
  GDU's to 50% Silk: 1408
B. Plant Characteristics:
  Plant height (to tassel tip): 269 cm
  Length of top ear internode: 15 cm
  Number of ears per stalk: Single
  Ear height (to base of top ear): 110 cm
  Number of tillers: None
  Cytoplasm type: Normal
C. Leaf:
  Color: Dark Green (B14)
  Angle from Stalk: <30 degrees
  Marginal Waves: Few (WF9)
  Number of Leaves (mature plants): 18
  Sheath Pubescence: Light (W22)
  Longitudinal Creases: Few (OH56A)
  Length (Ear node leaf): 89 cm
  Width (widest point, ear node leaf): 10 cm
D. Tassel:
  Number lateral branches: 6
  Branch Angle from central spike: <30 degrees
  Pollen Shed: Heavy (KY21)
  Peduncle Length (top leaf to basal branches): 18 cm
  Anther Color: Pink
  Glume Color: Green
E. Ear (Husked Ear Data Except When Stated Otherwise):
  Length: 18 cm
  Weight: 249 gm
  Mid-point Diameter: 50 mm
  Silk Color: Yellow
  Husk Extension (Harvest stage): Medium (Barely covering ear)
  Husk Leaf: Long (>15 cm)
  Taper of Ear: Slight
  Position of Shank (dry husks): Horizontal
  Kernel Rows: Slight, Distinct Number = 18
  Husk Color (fresh): Light Green
  Husk Color (dry): Buff
  Shank Length: 16 cm
  Shank (No. of internodes): 9
F. Kernel (Dried):
  Size (from ear mid-point)
    Length: 14 mm
    Width: 8 mm
    Thick: 4 mm
  Shape Grade (% rounds): <20
  Pericarp Color: Colorless
  Aleurone Color: Homozygous Yellow
  Endosperm Color: Yellow
  Endosperm Type: Normal Starch
  Gm Wt/100 Seeds (unsized): 32 gm
G. Cob:
  Diameter at mid-point: 25 mm
  Strength: Strong
  Color: Red
H. Diseases:
  Corn Lethal Necrosis (MCMV = Maize Chlorotic mottle virus and MDMV = Maize Dwarf Mosaic Virus): Intermediate
  Anthracnose Stalk Rot (*C. graminicola*): Intermediate
  N. Leaf Blight (*E. turcicum*): Resistant
  Gray Leaf Spot (*C. zeae*): Susceptible
  Goss's Wilt (*C. nebraskense*): Highly Resistant
  Fusarium Ear Hold (*F. moniliforme*): Resistant
  Gibberella Ear Rot (*G. zeae*): Resistant
I. Insects:
  European Corn Borer-1 Leaf Damage (Preflowering): Susceptible
  European Corn Borer-2 (Post-flowering): Susceptible
  The above descriptions are based on a scale of 1-9, 1 being highly susceptible, 9 being highly resistant.
  S (Susceptible): A score of 1-3.
  I (Intermediate): A score of 4-5.
  R (Resistant): A score of 6-7.
  H (Highly Resistant): a score of 8-9. Highly resistant does not imply the hybred is immune.
J. Variety Most Closely Resembling:
  Character     Hybrid
  Maturity      Pioneer Brand 3417
  Usage         Pioneer Brand 3417

This invention also relates to the use of 3525 in producing three-way and double-cross hybrids.

The terms variant, trivial modification, and mutant refer to a hybrid seed or a plant produced by that hybrid seed which is phenotypically similar to 3525 with the exception of one or two monogenic traits, or which has a genome which is ≧90% identical to 3525 by RFLP analysis.

As used herein, the term "plant" includes plant cells, plant protoplasts, plant cell or tissue culture from which corn plants can be regenerated, plant calli, plant clumps and plant cells that are intact in plants or parts of plants, such as flowers, kernels, ears, cobs, leaves, husks, stalks and the like.

Tissue culture of corn is described in European Patent Application, publication number 160,390, incorporated herein by reference. Corn tissue culture procedures are also described in Green and Rhodes, "Plant Regeneration in Tissue Culture of Maize," *Maize for Biological Research,* (*Plant Molecular Biology Association,* Charlottesville, Va. 1982) at 367–372 and in Duncan, et al., "The Production of Callus Capable of Plant Regeneration from Immature Embryos of Numerous *Zea Mays* Genotypes," 165 *Planta* 322–332 (1985).

Duncan, Williams, Zehr, and Widholm, Planta, (1985) 165:322–332 reflects that 97% of the plants cultured which produced callus were capable of plant regeneration. Subsequent experiments with both inbreds and hybrids produced 91% regenerable callus which produced plants. In a further study in 1988, Songstad, Duncan & Widholm in *Plant Cell Reports* (1988), 7:262–265 reports several media additions which enhance regenerability of callus of two inbred lines. Other published reports also indicated that "nontraditional" tissues are capable of producing somatic embryogenesis and plant regeneration. K. P. Rao, et al., *Maize Genetics Cooperation Newsletter,* 60:64–65 (1986), refers to somatic embryogenesis from glume callus cultures and B. V. Conger, et al., *Plant Cell Reports,* 6:345–347 (1987) indicates somatic embryogenesis from the tissue cultures of maize leaf segments. Thus, it is clear from the literature that the state of the art is such that these methods of obtaining plants are, and were, "conventional" in the sense that they are routinely used and have a very high rate of success.

USES OF CORN

Corn is used as human food, livestock feed, and as raw material in industry. The food uses of corn, in addition to human consumption of corn kernels, include both products of dry- and wet-milling industries. The principal products of corn dry milling are grits, meal and flour. The corn wet-milling industry can provide starch, syrups, and dextrose for food use. Corn oil is recovered from corn germ, which is a by-product of both dry- and wet-milling industries.

Corn is also used extensively as livestock feed primarily to beef cattle, dairy cattle, hogs, and poultry.

Industrial uses of corn are mainly from corn starch in the wet-milling industry and corn flour in the dry-milling industry. The industrial applications of corn starch and flour are based on functional properties, such as viscosity, film formation, adhesive properties, and ability to suspend particles. Corn starch and flour have application in the paper and textile industries. Other industrial uses include applications in adhesives, building materials, foundry binders, laundry starches, explosives, oil-well muds, and other mining applications.

Plant parts other than the grain of corn are also used in industry. Stalks and husks are made into paper and wallboard and cobs are used for fuel, to make charcoal.

The seed of 3525, the hybrid corn plant produced from the seed, and various parts of the hybrid corn plant can be utilized for human food, livestock feed, and as a raw material in industry.

The plant of 3525 can be produced from seed of 3525, which is available to the public through Pioneer Hi-Bred International, Inc., Des Moines, Iowa. Alternatively, multiple plants can be produced from a single seed by germinating the seed to form a plant, culturing nodes from the plant as they form, and regenerating plants from the cultures, *ad infinitum.*

EXAMPLE 1

Research Comparisons for Pioneer Hybrid 3525

Comparisons of the characteristics for Pioneer Brand Hybrid 3525 were made against Pioneer Brand Hybrids 3417, 3398, 3394, 3379, and 3362; and Wyffels Brand Hybrid WYF627. These hybrids are grown in the Central and Eastern Corn Belt and have similar maturity. Table 1A compares Pioneer Brand Hybrid 3525 to Pioneer Brand Hybrid 3417. The results show 3525 has higher yield, lower grain harvest moisture, and similar test weight compared to 3417. 3525 has fewer barren plants and is a taller hybrid with higher ear placement than 3417. 3525 and 3417 have similar seedling vigor, but 3525 has a higher early stand count. 3525 flowers (GDU Shed and GDU Silk) later than 3417. 3525 has better grain appearance and stay green, similar stalk lodging resistance, more susceptibility to root lodging, and fewer brittle stalks than 3417.

The results in Table 1B show Pioneer Brand Hybrid 3525 has slightly higher yield and lower grain harvest moisture and test weight than Pioneer Brand Hybrid 3398. 3525 is a taller hybrid with higher ear placement and flowers (GDU Shed and GDU Silk) later than 3398. 3525 drops slightly more ears than 3398. 3525 and 3398 have similar grain appearance, but 3525 has better stay green. 3525 has better stalk lodging resistance and more susceptibility to root lodging than 3398.

Table 1C compares Pioneer Brand Hybrid 3525 to Pioneer Brand Hybrid 3394. The results show 3525 has lower yield, grain harvest moisture, and test weight than 3394. 3525 has fewer barren plants than 3394. 3525 is a taller hybrid with higher ear placement compared to 3394. 3525 and 3394 silk (GDU Silk) similarly, but 3525 sheds (GDU Shed) later. 3525 has better grain appearance and poorer stay green than 3394. 3525 is more susceptible to stalk and root lodging and has more brittle stalks than 3394.

The results in Table 1D, comparing Pioneer Brand Hybrid 3525 to Pioneer Brand Hybrid 3379, show 3525 has higher yield and lower grain harvest moisture and test weight than 3379. 3525 is taller and has higher ear placement than 3379. 3525 sheds (GDU Shed) later and silks (GDU Silk) earlier than 3379. 3525 has poorer stay green, more susceptibility to stalk and root lodging, and more brittle stalks than 3379.

Table 1E shows that Pioneer Brand Hybrid 3525 has higher yield, lower grain harvest moisture, and similar test weight compared to Pioneer Brand Hybrid 3362. 3525 is taller with higher ear placement and flowers (GDU Shed and GDU Silk) later than 3362. 3525 has better seedling vigor and a higher early stand count than 3362. 3525 has better grain appearance and stay green than 3362. 3525 has better stalk lodging resistance, more susceptibility to root lodging, and more brittle stalks than 3362.

Table 1F compares Pioneer Brand Hybrid 3525 to Wyffels Brand Hybrid WYF627. The data shows 3525 has higher yield and test weight and lower grain harvest moisture than WYF627. 3525 is taller with higher ear placement and flowers (GDU Shed and GDU Silk) later than WYF627. 3525 has better seedling vigor but a slightly lower early stand count than WYF627. 3525 has better grain appearance and stay green and is more resistant to stalk and root lodging than WYF627.

TABLE 1A

VARIETY #1 - 3525
VARIETY #2 - 3417

| DEPT | VAR # | BU ACR ABS | BU ACR % MN | MST ABS | BAR PLT ABS | PLT HT ABS | EAR HT ABS | SDG VGR ABS | EST CNT ABS | DRP EAR ABS |
|---|---|---|---|---|---|---|---|---|---|---|
| TOTAL SUM | 1 | 156.8 | 106 | 18.6 | 96.9 | 106.6 | 50.4 | 5.5 | 60.2 | 99.3 |
| | 2 | 154.5 | 104 | 19.8 | 95.2 | 97.6 | 39.6 | 5.5 | 59.1 | 99.7 |
| | LOCS | 303 | 303 | 303 | 23 | 151 | 151 | 117 | 169 | 242 |
| | REPS | 476 | 476 | 476 | 32 | 234 | 234 | 201 | 269 | 370 |
| | DIFF | 2.3 | 2 | 1.2 | 1.7 | 9.1 | 10.7 | 0.0 | 1.1 | 0.5 |
| | PROB | .039+ | .048+ | .000# | .118 | .000# | .000# | .930 | .023+ | .000# |

| DEPT | VAR # | GDU SHD ABS | GDU SLK ABS | TST WTA ABS | GRN APP ABS | STA GRN ABS | STK LDG ABS | RT LDG ABS | BRT STK ABS |
|---|---|---|---|---|---|---|---|---|---|
| TOTAL SUM | 1 | 1430 | 1412 | 57.3 | 7.1 | 5.8 | 92.8 | 93.1 | 96.4 |
| | 2 | 1361 | 1371 | 57.4 | 6.3 | 5.0 | 92.0 | 99.4 | 92.1 |
| | LOCS | 106 | 19 | 302 | 213 | 168 | 290 | 120 | 12 |
| | REPS | 151 | 32 | 475 | 322 | 262 | 440 | 183 | 18 |
| | DIFF | 69 | 41 | 0.1 | 0.8 | 0.8 | 0.9 | 6.3 | 4.2 |
| | PROB | .000# | .000# | .353 | .000# | .000# | .193 | .000# | .161 |

* = 10% SIG
+ = 5% SIG
# = 1% SIG

TABLE 1B

VARIETY #1 - 3525
VARIETY #2 - 3398

| DEPT | VAR # | BU ACR ABS | BU ACR % MN | MST ABS | BAR PLT ABS | PLT HT ABS | EAR HT ABS | SDG VGR ABS | EST CNT ABS | DRP EAR ABS |
|---|---|---|---|---|---|---|---|---|---|---|
| TOTAL SUM | 1 | 159.9 | 104 | 19.4 | 96.4 | 103.1 | 48.4 | 5.5 | 59.6 | 99.2 |
| | 2 | 158.1 | 104 | 21.3 | 98.0 | 93.5 | 39.3 | 5.3 | 58.7 | 99.7 |
| | LOCS | 132 | 132 | 132 | 5 | 68 | 68 | 57 | 84 | 106 |
| | REPS | 238 | 238 | 238 | 10 | 117 | 117 | 108 | 149 | 192 |
| | DIFF | 1.8 | 0 | 2.0 | 1.6 | 9.6 | 9.1 | 0.2 | 0.9 | 0.5 |
| | PROB | .327 | .882 | .000# | .498 | .000# | .000# | .358 | .130 | .078* |

| DEPT | VAR # | GDU SHD ABS | GDU SLK ABS | TST WTA ABS | GRN APP ABS | STA GRN ABS | STK LDG ABS | RT LDG ABS | BRT STK ABS |
|---|---|---|---|---|---|---|---|---|---|
| TOTAL SUM | 1 | 1423 | 1417 | 56.9 | 6.7 | 5.5 | 93.5 | 93.3 | 96.6 |
| | 2 | 1359 | 1379 | 57.3 | 6.6 | 4.4 | 91.3 | 97.7 | 96.2 |
| | LOCS | 34 | 9 | 132 | 65 | 70 | 125 | 53 | 7 |
| | REPS | 57 | 12 | 237 | 122 | 130 | 225 | 91 | 12 |
| | DIFF | 64 | 37 | 0.4 | 0.2 | 1.2 | 2.2 | 4.4 | 0.3 |
| | PROB | .000# | .002# | .000# | .281 | .000# | .074* | .005# | .891 |

* = 10% SIG
+ = 5% SIG
# = 1% SIG

TABLE 1C

VARIETY #1 - 3525
VARIETY #2 - 3394

| DEPT | VAR # | BU ACR ABS | BU ACR % MN | MST ABS | BAR PLT ABS | PLT HT ABS | EAR HT ABS | SDG VGR ABS | EST CNT ABS | DRP EAR ABS |
|---|---|---|---|---|---|---|---|---|---|---|
| TOTAL SUM | 1 | 156.7 | 106 | 18.3 | 96.6 | 105.2 | 50.3 | 5.2 | 58.7 | 99.2 |
| | 2 | 159.7 | 108 | 19.8 | 95.2 | 99.4 | 47.1 | 6.2 | 58.6 | 99.4 |
| | LOCS | 274 | 274 | 274 | 20 | 144 | 144 | 105 | 169 | 235 |
| | REPS | 433 | 433 | 434 | 29 | 224 | 224 | 182 | 267 | 369 |
| | DIFF | 3.0 | 2 | 1.5 | 1.3 | 5.8 | 3.2 | 1.0 | 0.0 | 0.1 |
| | PROB | .003# | .005# | .000# | .086* | .000# | .000# | .000# | .895 | .355 |

| | VAR | GDU SHD | GDU SLK | TST WTA | GRN APP | STA GRN | STK LDG | RT LDG | BRT STK |
|---|---|---|---|---|---|---|---|---|---|

TABLE 1C-continued

| | VARIETY #1 - 3525 | | | | | | | |
|---|---|---|---|---|---|---|---|---|
| | VARIETY #2 - 3394 | | | | | | | |
| DEPT | # | ABS | ABS | ABS | ABS | ABS | ABS | ABS | ABS |
| TOTAL SUM | 1 | 1427 | 1413 | 57.4 | 7.1 | 5.4 | 92.1 | 92.9 | 96.6 |
| | 2 | 1416 | 1413 | 58.0 | 6.9 | 6.2 | 94.5 | 97.1 | 97.7 |
| | LOCS | 92 | 12 | 273 | 186 | 156 | 269 | 106 | 9 |
| | REPS | 127 | 16 | 433 | 286 | 249 | 423 | 164 | 14 |
| | DIFF | 1.1 | 0 | 0.6 | 0.3 | 0.8 | 2.4 | 4.1 | 1.1 |
| | PROB | .002# | .957 | .000# | .004# | .000# | .000# | .000# | .513 |

* = 10% SIG
+ = 5% SIG
# = 1% SIG

TABLE 1D

| | | VARIETY #1 - 3525 | | | | | | | |
|---|---|---|---|---|---|---|---|---|---|
| | | VARIETY #2 - 3379 | | | | | | | |
| DEPT | VAR # | BU ACR ABS | BU ACR % MN | MST ABS | BAR PLT ABS | PLT HT ABS | EAR HT ABS | SDG VGR ABS | EST CNT ABS | DRP EAR ABS |
| TOTAL SUM | 1 | 154.5 | 106 | 18.5 | 96.5 | 107.2 | 51.3 | 5.5 | 59.0 | 99.1 |
| | 2 | 150.2 | 103 | 20.5 | 96.1 | 103.6 | 48.2 | 5.4 | 59.3 | 99.3 |
| | LOCS | 225 | 225 | 225 | 19 | 119 | 119 | 102 | 147 | 191 |
| | REPS | 369 | 369 | 369 | 27 | 187 | 187 | 178 | 238 | 306 |
| | DIFF | 4.2 | 2 | 2.1 | 0.3 | 3.7 | 3.1 | 0.1 | 0.3 | 3 |
| | PROB | .001# | .019+ | .000# | .652 | .000# | .000# | .677 | .356 | .162 |

| DEPT | VAR # | GDU SHD ABS | GDU SLK ABS | TST WTA ABS | GRN APP ABS | STA GRN ABS | STK LDG ABS | RT LDG ABS | BRT STK ABS |
|---|---|---|---|---|---|---|---|---|---|
| TOTAL SUM | 1 | 1419 | 1406 | 57.3 | 7.0 | 5.3 | 91.4 | 93.8 | 97.3 |
| | 2 | 1408 | 1414 | 57.7 | 6.9 | 6.1 | 93.0 | 94.6 | 98.5 |
| | LOCS | 77 | 10 | 225 | 161 | 130 | 219 | 96 | 10 |
| | REPS | 109 | 13 | 369 | 256 | 206 | 355 | 149 | 17 |
| | DIFF | 11 | 0.8 | 0.5 | 0.2 | 0.8 | 1.5 | 0.8 | 1.2 |
| | PROB | .003# | .168 | .000# | .127 | .000# | .036+ | .284 | .319 |

* = 10% SIG
+ = 5% SIG
# = 1% SIG

TABLE 1E

| | | VARIETY #1 - 3525 | | | | | | | |
|---|---|---|---|---|---|---|---|---|---|
| | | VARIETY #2 - 3362 | | | | | | | |
| DEPT | VAR # | BU ACR ABS | BU ACR % MN | MST ABS | BAR PLT ABS | PLT HT ABS | EAR HT ABS | SDG VGR ABS | EST CNT ABS | DRP EAR ABS |
| TOTAL SUM | 1 | 155.3 | 105 | 18.8 | 96.7 | 103.4 | 50.0 | 5.5 | 61.1 | 99.3 |
| | 2 | 148.1 | 101 | 20.5 | 97.6 | 95.2 | 44.0 | 4.9 | 59.1 | 99.3 |
| | LOCS | 159 | 159 | 159 | 8 | 77 | 77 | 78 | 96 | 129 |
| | REPS | 280 | 280 | 280 | 14 | 132 | 132 | 142 | 167 | 219 |
| | DIFF | 7.2 | 4 | 1.7 | 0.9 | 8.2 | 5.9 | 0.6 | 2.0 | 0.1 |
| | PROB | .000# | .001# | .000# | .512 | .000# | .000# | .000# | .001# | .569 |

| DEPT | VAR # | GDU SHD ABS | GDU SLK ABS | TST WTA ABS | GRN APP ABS | STA GRN ABS | STK LDG ABS | RT LDG ABS | BRT STK ABS |
|---|---|---|---|---|---|---|---|---|---|
| TOTAL SUM | 1 | 1424 | 1412 | 56.9 | 7.1 | 5.5 | 92.0 | 94.4 | 96.6 |
| | 2 | 1392 | 1406 | 56.9 | 6.6 | 5.3 | 90.9 | 97.1 | 99.0 |
| | LOCS | 46 | 9 | 159 | 94 | 83 | 153 | 72 | 9 |
| | REPS | 74 | 11 | 280 | 166 | 145 | 267 | 118 | 14 |
| | DIFF | 32 | 7 | 0.0 | 0.4 | 0.2 | 1.1 | 2.7 | 2.3 |
| | PROB | .000# | .397 | .015 | .000# | .262 | .186 | .006# | .175 |

* = 10% SIG
+ = 5% SIG
# = 1% SIG

TABLE 1F

VARIETY #1 - 3525
VARIETY #2 - WYF627

| DEPT | VAR # | BU ACR ABS | BU ACR % MN | MST ABS | PLT HT ABS | EAR HT ABS | SDG VGR ABS | EST CNT ABS | DRP EAR ABS | GDU SHD ABS |
|---|---|---|---|---|---|---|---|---|---|---|
| TOTAL SUM | 1 | 155.4 | 108 | 18.5 | 111.3 | 53.8 | 6.3 | 58.4 | 99.0 | 1401 |
| | 2 | 144.1 | 99 | 20.3 | 105.9 | 48.9 | 5.4 | 60.0 | 99.4 | 1359 |
| | LOCS | 69 | 69 | 69 | 31 | 31 | 15 | 47 | 59 | 23 |
| | REPS | 111 | 111 | 111 | 43 | 43 | 27 | 69 | 89 | 30 |
| | DIFF | 11.3 | 9 | 1.8 | 5.5 | 5.5 | 0.9 | 1.6 | 0.3 | 42 |
| | PROB | .000# | .001# | .000# | .000# | .000# | .010+ | .104 | .100 | .000# |

| DEPT | VAR # | GDU SLK ABS | TST WTA ABS | GRN APP ABS | STA GRN ABS | STK LDG ABS | RT LDG ABS | BRT STK ABS |
|---|---|---|---|---|---|---|---|---|
| TOTAL SUM | 1 | 1410 | 57.1 | 7.1 | 5.6 | 92.1 | 96.5 | 99.2 |
| | 2 | 1375 | 56.9 | 6.3 | 3.8 | 88.8 | 98.0 | 100.0 |
| | LOCS | 2 | 68 | 49 | 36 | 70 | 35 | 1 |
| | REPS | 2 | 110 | 75 | 51 | 111 | 50 | 2 |
| | DIFF | 35 | 0.2 | 0.8 | 1.8 | 3.3 | 1.5 | 0.8 |
| | PROB | .090* | .150 | .000# | .000# | .043+ | .201 | |

* = 10% SIG
+ = 5% SIG
# = 1% SIG

EXAMPLE 2

Strip Test Data for Hybrid 3525

Comparison data was collected from strip tests that were grown by farmers. Each hybrid was grown in strips of 4, 6, 8, 12, etc. rows in fields depending upon the size of the planter used. The data was collected from strip tests that had the hybrids in the same area and weighed. The moisture percentage was determined and bushels per acre was adjusted to 15.5 percent moisture. The number of comparisons represent the number of location or replications for the two hybrids that were grown in the same field in close proximity and compared.

Comparison strip testing was done between Pioneer Brand Hybrid 3525 and Pioneer Brand Hybrids 3417, 3398, 3394, 3379, and 3362; and Wyffels Brand Hybrid WYF627. The comparisons came from all the hybrid's adapted growing areas in the United States.

These results are presented in Table 2. The results show 3525 has a yield advantage over Pioneer Brand Hybrids 3379, 3362, and Wyffels Brand Hybrid WYF627 and a yield disadvantage of 1.9, 2.4, and 1.8 bushels per acre to Pioneer Brand Hybrids 3417, 3398, and 3394, respectively. 3525 had a moisture advantage over all hybrids compared. 3525 showed a greater income advantage to the farmer based on adjusted gross income over all hybrids compared except Pioneer Brand Hybrids 3417 and 3394 where the disadvantage was $0.44 and $0.71 per acre, respectively. In its area of adaptation, 3525 should be an important addition where these hybrids are grown.

TABLE 2

PIONEER HYBRID 3525 VS PIONEER HYBRIDS 3417, 3398, 3394, 3379, 3362, AND WYFFELS BRAND WYF627 FROM 1991 STRIP TESTS

| Brand | Product | Yield | Moist | Income/ Acre | Pop K/Acre | Stand (%) | Roots (%) | Test Wt |
|---|---|---|---|---|---|---|---|---|
| PIONEER | 3525 | 159.4 | 17.8 | 389.62 | 25.3 | 89 | 93 | 57.6 |
| PIONEER | 3417 | 161.3 | 19.2 | 390.06 | 25.3 | 88 | 96 | 57.2 |
| Advantage | | −1.9 | 1.4 | −0.44 | 0.0 | 1 | −3 | 0.4 |
| Number of Comparisons | | 335 | 335 | 335 | 190 | 156 | 127 | 252 |
| Percent Wins | | 42 | 86 | 48 | 40 | 41 | 10 | 55 |
| Probability of Difference | | 99 | 99 | 19 | 10 | 73 | 99 | 99 |
| PIONEER | 3525 | 165.9 | 15.7 | 411.30 | 24.8 | 89 | 93 | 58.3 |
| PIONEER | 3398 | 168.3 | 17.7 | 411.11 | 24.0 | 96 | 97 | 58.3 |
| Advantage | | −2.4 | 2.0 | 0.19 | 0.8 | −7 | −4 | 0.0 |
| Number of Comparisons | | 60 | 60 | 60 | 32 | 23 | 14 | 60 |
| Percent Wins | | 40 | 98 | 46 | 50 | 17 | 0 | 36 |
| Probability of Difference | | 85 | 99 | 4 | 93 | 99 | 84 | 6 |
| PIONEER | 3525 | 150.4 | 17.6 | 368.45 | 25.1 | 89 | 93 | 57.9 |
| PIONEER | 3394 | 152.2 | 19.0 | 369.16 | 24.9 | 92 | 95 | 58.1 |
| Advantage | | −1.8 | 1.4 | −0.71 | 0.2 | −3 | −2 | −0.2 |
| Number of Comparisons | | 372 | 372 | 372 | 210 | 171 | 121 | 285 |
| Percent Wins | | 43 | 88 | 48 | 45 | 23 | 9 | 31 |
| Probability of Difference | | 99 | 99 | 31 | 69 | 99 | 96 | 97 |

TABLE 2-continued

PIONEER HYBRID 3525 VS PIONEER HYBRIDS 3417,
3398, 3394, 3379, 3362, AND WYFFELS BRAND WYF627
FROM 1991 STRIP TESTS

| Brand | Product | Yield | Moist | Income/Acre | Pop K/Acre | Stand (%) | Roots (%) | Test Wt |
|---|---|---|---|---|---|---|---|---|
| PIONEER | 3525 | 152.0 | 16.6 | 375.03 | 24.3 | 89 | 90 | 58.3 |
| PIONEER | 3379 | 150.4 | 18.6 | 365.92 | 24.2 | 92 | 91 | 58.3 |
| Advantage | | 1.6 | 2.0 | 9.11 | 0.1 | −3 | −1 | 0.0 |
| Number of Comparisons | | 205 | 205 | 205 | 88 | 63 | 40 | 145 |
| Percent Wins | | 54 | 89 | 61 | 45 | 17 | 15 | 40 |
| Probability of Difference | | 88 | 99 | 99 | 36 | 99 | 73 | 6 |
| PIONEER | 3525 | 156.0 | 16.7 | 384.58 | 24.5 | 88 | 92 | 58.3 |
| PIONEER | 3362 | 152.9 | 18.6 | 371.83 | 24.3 | 90 | 95 | 57.7 |
| Advantage | | 3.1 | 1.9 | 12.75 | 0.2 | −2 | −3 | 0.6 |
| Number of Comparisons | | 162 | 162 | 162 | 63 | 49 | 35 | 118 |
| Percent Wins | | 59 | 88 | 64 | 39 | 28 | 0 | 59 |
| Probability of Difference | | 99 | 99 | 99 | 69 | 87 | 96 | 99 |
| PIONEER | 3525 | 64.9 | 17.3 | 159.91 | 0.0 | 0 | 0 | 59.0 |
| WYFFELS | WYF627 | 50.8 | 18.4 | 124.05 | 0.0 | 0 | 0 | 58.0 |
| Advantage | | 14.1 | 1.1 | 35.86 | 0.0 | 0 | 0 | 1.0 |
| Number of Comparisons | | 1 | 1 | 1 | 0 | 0 | 0 | 1 |
| Percent Wins | | 100 | 100 | 100 | 0 | 0 | 0 | 100 |
| Probability of Difference | | 0 | 0 | 0 | 0 | 0 | 0 | 0 |
| PIONEER | 3525 | 154.4 | 17.2 | 379.15 | 24.9 | 89 | 93 | 58.0 |
| WEIGHTED AVG | | 154.5 | 18.8 | 374.89 | 24.8 | 90 | 95 | 57.8 |
| Advantage | | −0.1 | 1.6 | 4.26 | 0.1 | −1 | −2 | 0.2 |
| Number of Comparisons | | 1172 | 1172 | 1172 | 608 | 485 | 360 | 875 |
| Percent Wins | | 48 | 86 | 54 | 43 | 29 | 10 | 44 |
| Probability of Difference | | 4 | 99 | 99 | 83 | 99 | 99 | 99 |

NOTE: The probability values are useful in analyzing if there is a "real" difference in the genetic potential of the products involved. High values are desirable, with 95% considered significant for real differences.

EXAMPLE 3

Comparison of Key Characteristics for Hybrid 3525

Characteristics of Pioneer Brand Hybrid 3525 are compared to Pioneer Brand Hybrids 3417, 3398, 3394, 3379, and 3362; and Wyffels Brand Hybrid WYF627 in Table 3. The ratings given for most of the traits are on a 1–9 basis. In these cases 9 would be outstanding while 1 would be poor for the given characteristics. These values are based on performance of a given hybrid relative to other Pioneer commercial, precommercial, and competitive hybrids that are grown in research and strip test trials. The traits characterized in Table 3 were defined previously and the ratings utilized not only research data, but experience trained corn researchers had in the field as well as sales experience with the hybrids in strip tests and the field. These scores reflect the hybrid's relative performance to other hybrids for the characteristics listed. The table shows 3525 yielded well for its maturity. Relative to the other hybrids, 3525 has very good stay green. With the exception of 3394, 3525 is a taller hybrid with higher ear placement. 3525 has overall excellent yield and agronomic characteristics which should make it an important hybrid in its area of adaptation.

TABLE 3

HYBRID PATENT COMPARISONS--CHARACTERISTICS
Pioneer Hybrid 3525 vs Pioneer Hybrid 3417, 3398, 3394, 3379, 3362, and Wyffels Brand Hybrid WYF627

| HYBRID | SILK CRM | GDU SILK | BL CRM | GDU BL | CRM | YLD | H/POP | L/POP | D/D |
|---|---|---|---|---|---|---|---|---|---|
| 3525 | 111 | 1408 | 106 | 2642 | 106 | 9 | 9 | 8 | 5 |
| 3417 | 108 | 1382 | 111 | 2199 | 108 | 9 | 8 | 9 | 6 |
| 3398 | 109 | 1381 | 111 | 2797 | 111 | 9 | 8 | 9 | 5 |
| 3394 | 112 | 1428 | 110 | 2796 | 111 | 9 | 9 | 9 | 6 |
| 3379 | 113 | 1433 | 114 | 2907 | 111 | 8 | 9 | 6 | 8 |
| 3362 | 111 | 1418 | 110 | 2808 | 111 | 8 | 9 | 6 | 1 |
| WYF627 | 108 | 1435 | 108 | 2739 | 111 | 7 | 5 | 3 | 5 |

| HYBRID | S/L | R/L | STGR | D/T | T/WT | G/A | S/V | P/HT | E/HT | D/E | B/STK |
|---|---|---|---|---|---|---|---|---|---|---|---|
| 3525 | 5 | 5 | 8 | 5 | 5 | 5 | 7 | 7 | 7 | 6 | 5 |
| 3417 | 4 | 6 | 4 | 8 | 5 | 5 | 5 | 4 | 2 | 6 | 4 |
| 3398 | 6 | 6 | 3 | 8 | 5 | 7 | 5 | 4 | 3 | 6 | 6 |
| 3394 | 7 | 1 | 8 | 7 | 5 | 6 | 8 | 5 | 4 | 4 | 4 |
| 3379 | 7 | 5 | 7 | 8 | 5 | 5 | 4 | 4 | 5 | 6 | 7 |
| 3362 | 1 | 1 | 1 | 9 | 4 | 4 | 4 | 4 | 3 | 6 | 8 |
| WYF627 | 3 | 3 | 2 | 4 | 4 | 4 | 4 | 4 | 5 | 4 | — |

Although the foregoing invention has been described in some detail by way of illustration and example for purposes of clarity and understanding, it will be obvious that certain changes and modifications may be practiced within the scope of the invention, as limited only by the scope of the appended claims.

Deposits

Applicants have made available to the public without restriction a deposit of at least 2500 seeds of Hybrid Corn Seed 3525 with the American Type Culture Collection (ATCC), Rockville, Md. 20852 USA, ATCC Deposit No. 97152. The seeds deposited with the ATCC are taken from the same deposit maintained by Pioneer Hi-Bred International, Inc., 700 Capital Square, 400 Locust Street, Des Moines, Iowa 50309 since prior to the filing date of this application. This deposit of the Hybrid Corn Seed 3525 will be maintained without restriction in the ATCC depository, which is a public depository, for a period of 30 years, or 5 years after the most recent request, or for the effective life of the patent, whichever is longer, and will be replaced if it becomes nonviable during that period.

What is claimed is:

1. A hybrid corn plant designated as 3525 produced from seed having ATCC accession No. 97152, and plant parts.

2. A tissue culture of regenerable cells of a hybrid corn plant designated as 3525 and produced from seed having ATCC accession No. 97152 wherein the plants regenerated from the culture have all the physiological and morphological characteristics of 3525.

3. A hybrid corn plant and its plant parts having all of the physiological and morphological characteristics of 3525, and produced from seed having ATCC accession No. 97152.

4. A tissue culture of a plant according to claim 2 wherein the tissue is selected from the group consisting of leaves, pollen, embryos, roots, root tips, anthers, silk, flowers, kernels, ears, cobs, husks, stalks, and cells thereof, and protoplasts.

5. A corn plant regenerated from the tissue culture of claim 2, and its plant pads, said plant possessing all the physiological and morphological characteristics of the hybrid 3525 produced from seed having ATCC accession No. 97152.

* * * * *